(12) United States Patent
Duffield (10) Patent No.: US 10,293,069 B2
(45) Date of Patent: May 21, 2019

(54) DEVICE FOR EVAPORATING A VOLATILE FLUID

(71) Applicant: Reckitt Benckiser (Brands) Limited, Slough, Berkshire (GB)

(72) Inventor: Paul John Duffield, Beverley (GB)

(73) Assignee: RECKITT BENCKISER (BRANDS) LIMITED, Slough, Berkshire (GB)

( * ) Notice: Subject to any disclaimer, the term of this patent is extended or adjusted under 35 U.S.C. 154(b) by 0 days.

(21) Appl. No.: 16/008,565

(22) Filed: Jun. 14, 2018

(65) Prior Publication Data

US 2018/0289849 A1   Oct. 11, 2018

Related U.S. Application Data

(62) Division of application No. 14/907,126, filed as application No. PCT/GB2014/052424 on Aug. 7, 2014, now Pat. No. 10,071,179.

(30) Foreign Application Priority Data

Aug. 7, 2013   (GB) .................................. 1314117.1

(51) Int. Cl.
   *A61L 9/03*   (2006.01)
   *A01M 1/20*   (2006.01)

(52) U.S. Cl.
   CPC .......... *A61L 9/037* (2013.01); *A01M 1/2044* (2013.01); *A01M 1/2061* (2013.01); *A61L 2209/133* (2013.01); *A61L 2209/135* (2013.01)

(58) Field of Classification Search
   CPC ... A01M 1/2044; A01M 1/2061; A61L 9/037; A61L 2209/133; A61L 2209/135
   (Continued)

(56) References Cited

U.S. PATENT DOCUMENTS 9,743,463 B2   8/2017 Laghi et al.
9,877,359 B2 * 1/2018 Duffield .............. A01M 1/2061
(Continued)

FOREIGN PATENT DOCUMENTS

WO   9527411 A1   10/1995
WO   2007101298 A1   9/2007
(Continued)

OTHER PUBLICATIONS

International Search Report for corresponding application PCT/GB2014/052424 dated Oct. 27, 2014.
(Continued)

*Primary Examiner* — Charles S Bushey
(74) *Attorney, Agent, or Firm* — Norris McLaughlin, PA

(57) ABSTRACT

An assembly for evaporating a volatile fluid is described, the assembly including a device and a refill which are detachable from one another:

wherein the device includes a magnetic induction coil configured to operate with an alternating current passed therethrough at a frequency of between substantially 20 KHz to substantially 500 KHz and a volatile fluid transport part receiving area containing at least one piece of heat-conducting, non-magnetic metal foil and/or deposited heat-conducting, non-magnetic metal;

and wherein the refill includes a reservoir for the volatile fluid, a volatile fluid transport part to draw the fluid from the reservoir, and at least one magnetic susceptor having a coercivity of substantially 50 ampere/meter ($H_c$) to substantially 1500 ampere/meter ($H_c$).arranged to heat the wick predominately by magnetic hysteresis when an alternating current is passed through the induction coil, wherein the refill is attached to the device such that at least one magnetic (Continued)

susceptor is at least partially located within the volatile fluid transport part receiving area. Refills, devices and methods of operation are also described.

9 Claims, 7 Drawing Sheets

(58) Field of Classification Search
USPC .......... 261/128, 142, 72.1, 104, DIG. 65
See application file for complete search history.

(56) References Cited

U.S. PATENT DOCUMENTS

| | | | |
|---|---|---|---|
| 9,924,566 B2* | 3/2018 | Duffield | A01M 1/2061 |
| 10,071,179 B2* | 9/2018 | Duffield | A01M 1/2044 |
| 2001/0053283 A1 | 12/2001 | Levine et al. | |
| 2008/0257880 A1* | 10/2008 | Brown | A01M 1/2077 |
| | | | 219/618 |
| 2009/0000620 A1 | 1/2009 | Virr | |
| 2011/0200381 A1 | 8/2011 | Bylsma et al. | |
| 2015/0157756 A1 | 6/2015 | Duffield et al. | |
| 2015/0195871 A1 | 7/2015 | Duffield et al. | |
| 2015/0223292 A1 | 8/2015 | Duffield et al. | |
| 2015/0250028 A1 | 9/2015 | Duffield et al. | |
| 2016/0158397 A1 | 6/2016 | Duffield | |

FOREIGN PATENT DOCUMENTS

| | | |
|---|---|---|
| WO | 2014023964 A1 | 2/2014 |
| WO | 2014023965 A1 | 2/2014 |
| WO | 2014023966 A1 | 2/2014 |
| WO | 2014023967 A1 | 2/2014 |

OTHER PUBLICATIONS

Written Opinion of the International Searching Authority for corresponding application PCT/GB2014/052424 dated Oct. 27, 2014.

* cited by examiner

DEVICE FOR EVAPORATING A VOLATILE FLUID

This is a Divisional patent application of U.S. Ser. No. 14/907,126, now U.S. Pat. No. 10,071,179, which in turn was an application filed under 35 U.S.C. 371 of PCT/GB2014/052424, which claims priority of GB 1314117.1 filed 7 Aug. 2013. The entirety of these three documents are herein incorporated by reference.

The present invention relates to a device for evaporating a volatile fluid, for example a fragrance, pesticide, or a medicament.

Devices are known for emitting volatile liquids into an atmosphere. In one known device, described in U.S. Patent Publication No. 2002/0146243, a device having a housing is provided with a container for the volatile liquid, a wick extending from the container and an annular electrical heater located in the vicinity of the distal end of the wick to accelerate the evaporation of the volatile liquid from the wick. The container and wick are conventionally provided as a removable refill and the device uses a positive temperature coefficient (PTC) thermistor as the electrical heater. The device also has an electric plug by which it is plugged into a wall socket.

However, the heater must be run at a high temperature in order to sufficiently heat the volatile liquid within the wick. Further, the position of the heater within the housing means that the heater heats the wick as well as the surrounding device housing which provides two distinct drawbacks. Firstly, high levels of power consumption are required to get the electrical heater up to a satisfactory operating temperature to heat the wick to the temperature at which the volatile liquid can be emanated. Secondly, the mass of such an electrical heater and the surrounding device housing typically holds residual heat for a prolonged period after power to the heater has ceased, as such if there is an appetite to modify the operation of the device, particularly to address anti-habituation concerns associated with the emanated volatile liquid, such known devices are inherently slow to respond as removing power from the heater does not appreciably slow the emanation rate due to the residual heat.

Another known device can be found in International Publication No. WO 2005/112510, which describes an induction heating apparatus for the dissemination of volatile liquids. The device has a base module and a separate reservoir containing the volatile liquid. The base module has an upwardly-projecting cylindrical portion within which is a primary induction coil. The base of the reservoir has a recess which fits over the cylindrical portion of the base, around which is a secondary induction coil composed of a short-circuited wire coil. When current is passed through the primary coil, the secondary coil heats up and thus heats the liquid to increase the rate of evaporation. However, this device heats all of the volatile liquid in the reservoir, resulting in a device which is slow to reach the ideal operating temperature and operates with high levels of power consumption. Further, the device will continue to emit vapour after it has been switched off as the liquid in the reservoir will retain considerable residual heat and will take quite some time to cool. Furthermore, if the volatile liquid is a fragrance, heating the entire reservoir can degrade the quality of the fragrance over the life of the refill.

With the known devices as well as the Applicant's co-pending applications condensation in the device can occur due to the absence of sufficient airflow therethrough and/or the device itself being cool during operation, it is an object of the present invention to address such drawbacks.

According to a first aspect of the present invention, there is provided an assembly for evaporating a volatile fluid, the assembly comprising a device and a refill which are detachable from one another:

wherein the device comprises a magnetic induction coil configured to operate with an alternating current passed therethrough at a frequency of between substantially 20 KHz to substantially 500 KHz and a volatile fluid transport means receiving area containing at least one piece of heat conducting, non-magnetic metal foil and/or deposited heat-conducting, non-magnetic metal; and wherein the refill comprises a reservoir for the volatile fluid, a volatile fluid transport means to draw the fluid from the reservoir, and at least one magnetic susceptor having a coercivity of substantially 50 ampere/meter ($H_c$) to substantially 1500 ampere/meter ($H_c$) arranged to heat the wick predominately by magnetic hysteresis when said alternating current is passed through the induction coil, wherein the refill is attached to the device such that at least one magnetic susceptor is at least partially located within the volatile fluid transport means receiving area.

In the context of the present invention the term volatile fluid transport means is used herein to refer to any physical fluid transport conduit that permits the fluid to flow away from the reservoir toward the susceptor(s) without the assistance of gravity or powered means, in other words relying on capillary action, osmotic transfer, wicking action or the like to transport the fluid. Therefore the volatile fluid transport means in the present invention may be a fibrous substance such as a cellulose wick or the like or the volatile fluid transport means could be a porous substance such as ceramic wick or the like. Alternatively the volatile fluid transport means may be a gel matrix or the like, and in this arrangement the reservoir and the volatile fluid transport means may be made from the same material and/or may be substantially integral with each other.

Preferably the volatile fluid transport means protrudes through a cap in the refill to extend into the environment surrounding the refill distal from the reservoir. At least one of said magnetic susceptors may be provided in contact with the volatile fluid transport means in a distal portion thereof between the cap and the distal end of said means.

Preferably the volatile fluid transport means receiving area is provided in the form of a chimney comprising a substantially cylindrical component open at one end to receive the volatile fluid transport means and open at the other end to the environment surrounding the device. The chimney may be rotatable and/or movable relative to the rest of the device and/or may be provided with one or more holes and/or windows any or all of which may be arranged to promote airflow into the chimney and out into the environment surrounding the device.

The heat-conducting, non-magnetic metal may be selected from any suitable non-ferrous metal. Preferably the heat-conducting, non-magnetic metal is selected from a metal readily available in sheet foil form. Particularly preferably the heat-conducting, non-magnetic metal is selected from one of aluminium, silver, gold, platinum, tungsten, magnesium or copper. Most preferably the heat-conducting, non-magnetic metal is aluminium, of which aluminium foil is the preferred form. The aluminium sheet foil may be provided at any suitable thickness, although a thickness of between substantially 8 µm to substantially 25 µm is most preferred. The deposited heat-conducting, non-magnetic metal is preferably vacuum metalised deposited at a suitable thickness, although a thickness of between substantially 0.1 µm to substantially 10 µm is preferred.

The heat-conducting, non-magnetic metal will hereinafter be referred to solely as "aluminium" for the sake of brevity but it is to be understood that the inventor does not intend for this to be limiting on the invention disclosed herein, in other words, whilst aluminium is the most preferred heat-conducting, non-magnetic metal all subsequent references to "aluminium" are to be construed as relating to any suitable non-ferrous metal that is heat-conducting and non-magnetic.

The aluminium may be provided in contact with the inner surface of the chimney in order to face the volatile fluid transport means.

The deployment of aluminium foil and/or deposited aluminium is considered advantageous as it can reduce condensation in operation of the device by imparting heat to the volatile fluid transport means receiving area to reduce any temperature differential between the evaporated fluid and said area as well as creating a temperature gradient in the device to promote air currents through the device to improve the emanation of the evaporated fluid.

One key benefit of the deployment of aluminium foil and/or deposited aluminium compared to using either an additional magnetic susceptor within the device around the volatile fluid transport means receiving area or even a standard PTC thermistor is that the aluminium foil and/or deposited aluminium will not heat up by any appreciable or effective amount when exposed to the changing magnetic field induced by the induction coil as aluminium is non-magnetic and therefore is not capable of undergoing magnetic hysteresis. Furthermore, aluminium is very poor at eddy current heating. However, the aluminium in the device may heat up considerably when a refill containing a magnetic susceptor is attached to the device such that the magnetic susceptor is within the induced magnetic field. Whilst not wishing to be bound by the following proposed hypothesis, the inventor of the present invention suspects that when the magnetic susceptor in the refill is present in the induced magnetic field the susceptor has such an affinity for the induced magnetic field that it can force the magnetic field to be drawn through the aluminium and in doing so causes the aluminium to heat up. By selecting to correct quantity and location for the aluminium it is possible for the aluminium to heat to within approximately 5° C. of the susceptor temperature.

A further a key benefit of this arrangement is that the aluminium carries little mass and, therefore, has little ability to retain heat. Whereas the use of an additional magnetic susceptor within the device around the volatile fluid transport means receiving area or a standard PTC thermistor could be used to impart heat in the absence of a refill and fora period of time after the alternating current is stopped, the aluminium would rapidly dispose of its residual heat thus ensuring that the device remains cool to the touch post-use and thus improving its safety. With this arrangement, the susceptor(s) does not need to be connected to any part of the device, only to the volatile fluid transport means in the refill. This means that no electrical connection needs to pass through the reservoir to the susceptor(s) eliminating the possibility of a resultant fluid leakage path.

As the susceptor(s) is magnetic the susceptor(s) is predominately heated by magnetic hysteresis, and although some secondary eddy current heating may occur any eddy current heating is <50% of the heat generated in the magnetic susceptor(s), and preferably <40% of the heat generated in the magnetic susceptor(s) is from secondary eddy currents, and more preferably <35% of the heat generated in the magnetic susceptor(s) is from secondary eddy currents, and most preferably less than <30% of the heat generated in the magnetic susceptor(s) is from secondary eddy currents.

Hitherto the present invention the use of magnetic hysteresis as the predominant mechanism of heating has not been explored, the explored "induction heating" mechanism is eddy current heating. In an eddy current heating system it is ultimately the resistance of the target (i.e. the susceptor) which is responsible for the dissipation of power as heat. Preferably the electrical resistance of the target is low and the external induction field induces many tiny voltages in the target. As the resistance is low, the current circulating in the target material is huge, hence heat is produced. However the induced eddy current can also be used to do other forms of work instead of just producing heat, such as charging batteries for example.

Efficient transfer of electrical current through an air gap or other thermally insulating medium is fundamental to many applications of induction. The induced current can be used to produce resistive heating via eddy currents in a target on the opposite side of a thermally insulating material (e.g. air). Although induction heating applications are well known they have largely been applied to large white goods (e.g. Induction Hobs for cooking) or industrial processes (e.g. Furnaces). In these applications, despite the relatively high power levels and frequencies needed, induction offers cost and efficiency advantages over more traditional methods (e.g. resistive or joule heating) due to its inherent ability to effectively cross insulating layers. However the associated cost and complexity would be uneconomical where smaller amounts of heat are required or where such conditions do not exist.

One unwanted side effect of such eddy current induction processes is that some secondary magnetic hysteresis occurs which imparts a relatively small amount of generated heat. Heat generated by magnetic hysteresis is largely undesirable in transformers, power supplies and the like. As such most of the research and development work has been around how to prevent this secondary effect which produces heat.

In magnetic hysteresis heating the resistance of the target (i.e. susceptor) is unimportant and any circulating eddy currents which might occur do not represent a significant contribution to heating of the target, as the mechanism is fundamentally different. During magnetic hysteresis heating the magnetic domains within the target align themselves with the external field. When the polarity of the external field is reversed the magnetic domains reverse and realign themselves with the new field direction and it is this continued motion of the magnetic domains that produces the heat. At low power and relatively low frequencies this mechanism can be made to dominate by selection of an appropriate target.

For example, copper is non-magnetic and when copper is used in a refill as a non-magnetic susceptor in place of the magnetic susceptor as called for in the present invention, when the alternating current passed through the induction coil in the device is 150 KHz the copper susceptor merely heats by approximately 4° C. which is due solely to Eddy current heating. In contrast when the susceptor is magnetic and has a coercivity between substantially 50-1500 $H_C$ then under the same induction coil conditions the magnetic susceptor heats to at least 10× greater than the non-magnetic copper susceptor.

Preferably the magnetic susceptor(s) is made from at least one of the following materials: cast iron (annealed); nickel; nickel-coated steel; cobalt; carbon steel (annealed) 1% C; constructional steel particularly (0.3% C, 1% Ni) and/or (0.4% C, 3% Ni, 1.5% Cr); cobalt-iron alloy, particularly Permendur 24 (24% Co) and Permendur 49 (49% Co); Heusler alloy (61% Cu, 26% Mn, 13% Al); tool steel; powdered iron (preferably set in a resin base or the like to permit convenient shaping); iron filings (preferably set in a resin base or the like to permit convenient shaping).

Since the energy input to the assembly can be effectively targeted to heat the susceptor(s) within the induced magnetic field, only the susceptor(s) and the surrounding fluid in the volatile fluid transport means is heated rather than the energy being wasted as heat elsewhere in the refill and/or device as with the prior art assemblies. Further, as the susceptor(s) is a simple, low-cost component, it can be cost efficiently provided as part of a refill.

In a preferred arrangement each refill may be provided with at least one susceptor having heating characteristics which are optimised for the specific fluid contained in the refill, without the need for user intervention or complex control. For instance, it may be preferable to make the device as inexpensively as possible, therefore, one option to facilitate inexpensive manufacture would be to provide the device without any user-operable controls which permit a variation of its operating parameters such that the device operates in accordance with a single set of operating parameters. In this arrangement the length and/or mass and/or composition of the susceptor(s) in the refill may be varied to tune the heat achieved when the susceptor(s) is located within the induced magnetic field during use to the evaporation temperature of the volatile fluid. By way of example, where the volatile fluid is a fragrance composition fragrances are generally composed of a combination of top notes, middle notes and base notes. Top notes represent the most volatile part of the fragrance composition, these notes are usually perceived first by a human nose and include the "light" or "fresh" olfactive notes of the composition. The middle notes typically represent the "heart" of the mixture as they often provide the majority of the fragrance. The base notes are typically the least volatile part of the mixture and includes the heaviest molecules such as the notes that provide "rich" or "deep" olfactive notes of the composition. Due to their weight and size the base notes usually linger for the longest period. A fragrance mixture is typically made up of 10% top notes, 60% middle notes and 30% base notes. However, if it is desired to sell a fragrance made up predominantly of top notes it would be possible to deploy a refill containing a susceptor that heats to a relatively low temperature to ensure that the highly volatile top notes do not flash off to impart a user-desirable lifetime to the refill. Conversely if it is desired to sell a fragrance made up predominantly of base notes it would be possible to deploy a refill containing a susceptor(s) that heats to a relatively high temperature to ensure that the less volatile base notes are evaporated at a satisfactory rate to be noticeable by the user as well as imparting a user-desirable lifetime to the refill, i.e. a refill that will not last too long and risk clogging or blocking the volatile fluid transport means.

Furthermore, this preferred arrangement would make it permissible to market refills containing markedly different formulations for use with the same device. For instance, when evaporating fragrance formulations the preferred operating temperature may be in the order of 55-85° C. depending on the ratio of top, middle and base notes thereof, whereas for a pest control formulation much higher operating temperatures are generally required, typically in the order of 120-140° C. Accordingly an assembly according to the present invention may provide a user with a much simpler and inexpensive solution to emanate volatile fluids; simpler as the device can be left in situ and the desired refill may be changed by the user without the user having to communicate to the device that the refill contains a different formulation; inexpensive as a user need only purchase one device to emanate a wide variety of refills containing different formulations and the device need not have expensive nor complex refill recognition components to determine the device operating parameters.

Although one option to facilitate inexpensive manufacture of a device would be to provide the device without any user-operable controls which permit a variation of its operating parameters, it may be preferable to provide the device with basic user-operable controls which permit limited variation of the operating parameters, say between 2-4 predetermined operating parameters since some users may wish to change the intensity of the evaporated volatile fluid depending of the type of volatile fluid, the size of the space the fluid is being emanated into, etc.

Alternatively where producing the device as inexpensively as possible is less of a concern the device may be provided with one or more user-controllable inputs to permit the user to alter one or more operating parameters of the device to provide the user with a multitude of options to impart an emanation performance of the volatile fluid that they desire.

A further benefit of the assembly according to the present invention is that the mass of the components being heated is lower than hitherto available assemblies such that there will be a reduced amount of residual heat in said heated components during use and once the input energy to the assembly stops. This is particularly advantageous for several reasons, firstly, this improves the safety of the assembly during operation since only a small proportion of the device and/or refill will be heated thus making the assembly cool to the touch during use. Secondly, if there is the need to vary the emanation rate of the volatile fluid it is possible to rapidly cease emanation of the volatile fluid by removing the input power to the induction coil and/or modifying the duty cycle to impart a rapid cool down of the susceptor. For instance, when concerned with addressing anti-habituation during fragrance emanation it is necessary to allow a user's olfactive receptors to become non-saturated with the particular fragrance molecule(s) and this can only be achieved by ceasing the emanation of those fragrance molecule(s) and/or emanating a different fragrance. The ability of the device of the present invention to achieve rapid cool-down facilitates more rapid attenuation of the saturated olfactive receptors.

To provide the device with a stable maximum operating temperature the susceptor(s), may comprise a material with a stable Curie temperature, preferably less than 150° C. When the magnetic susceptor(s) is heated beyond this temperature, the susceptor(s) will become paramagnetic and no longer be susceptible to hysteresis heating until such time it cools down back below its Curie temperature. By selecting a magnetic susceptor(s) with a low and stable Curie temperature, it is possible to prevent the temperature of the volatile liquid in the volatile fluid transport means exceeding a predetermined level, even if for some reason excess power is supplied to the induction coil.

The susceptor(s) is preferably provided in direct contact with the volatile fluid transport means. In some embodiments the susceptor(s) may be at least partially embedded within the volatile fluid transport means. Alternatively or additionally, the susceptor(s) may surround a portion of the volatile fluid transport means. Most preferably however, the susceptor(s) is entirely embedded within the volatile fluid transport means.

One advantage of enclosing/embedding the susceptor(s) entirely within the volatile fluid transport means is that the heat emitted from the susceptor(s) is more effectively transferred to the adjacent fluid in the volatile fluid transport means, and not to the entirety of the volatile fluid transport means to some or all of the fluid reservoir. This is advantageous as where the volatile fluid is a fragrance, a medicament, a pest control material or an active pharmaceutical Ingredient, heating the entire reservoir can degrade the quality of the fluid over the life of the refill which is clearly undesirable.

Enclosing the susceptor(s) entirely within the volatile fluid transport means also minimises the potential for injury as the susceptor is less accessible and therefore is less likely to be accidently touched during use.

To ensure the heat generation within the susceptor(s) is as efficient as possible, the susceptor(s) may be at least partially located inside the induction coil during the operation of the assembly.

In a preferred embodiment the refill is provided with a single magnetic susceptor.

Alternatively the refill may be provided with more than one magnetic susceptor. In this arrangement by increasing the number of susceptors it is possible to increase the amount of heat generated within the same device operating parameters relative to when only a single susceptor is present. For example, where under fixed device operating parameters one magnetic susceptor is heated to 80° C. it is surprisingly found that if two identical susceptors are in the induced field rather than both heating to 80° C. they will both heat to 90° C. Furthermore, it is surprisingly found that if three identical susceptors are in the induced field rather than both heating to 80° C. or 90° C. they will both heat to 105° C. Whilst not wishing to be bound by the following proposed hypothesis, the inventor of the present invention suspects that the presence of multiple susceptors within the induced field focuses the field to the inside of the coil which decreases the area over which the field is spread thus increasing the magnetic focus and efficiency thereof.

In some embodiments, the device may further comprise a control unit to control the operation of the induction coil. In such an embodiment, the device may further comprise a feedback coil configured to interact with a magnetic field generated by the induction coil. Preferably the feedback coil is provided in the form of feedback windings turned around the induction coil, most preferably about 12 windings around the primary coil. In this arrangement the control unit may be configured to process an output from the feedback coil and, from this output, vary one or more operating parameters of the induction coil. The feedback coil is preferably configured to be capable of changing its output, in use, when a susceptor(s) is within the magnetic field of the induction coil.

Preferably the feedback coil in may be configured, in use, to change its output when one property of a susceptor is changed from refill to refill, for example if the shape or mass or material or surface area of the susceptor changes. The control unit may then be configured to interpret the change in output from the feedback coil to determine what type of refill is within the magnetic field of the induction coil, and from this, automatically vary a property of the induction coil to apply the appropriate heating regime to each particular refill.

To ensure the control unit is as simple as possible, thus as inexpensive as possible, the assembly is preferably configured such that the feedback coil only has to change its output in response to a change of a single property of the susceptor from refill to refill, therefore, it is preferred for refills configured to be used with such a device to have three of the following susceptor properties fixed and one of the following susceptor properties variable for detection of this variance by the feedback coil, wherein said susceptor properties are: shape; mass; material and surface area.

The provision of a feedback coil could also be used to prevent the susceptor(s) from getting too hot during use. As the susceptor(s) gets hot, the output from the feedback coil changes. The control unit could be configured to interpret a high temperature of the susceptor(s) based on this output, and from this, automatically vary a property of the induction coil to cool the susceptor.

A further use for the feedback coil the device could be to ensure that the device is operating as efficiently as possible, in this preferred arrangement the control unit monitors the output of the feedback coil to alter the duty cycle as required to ensure the current supplied through the induction coil is optimised to the particular susceptor(s) in proximity with the induction coil.

Examples of the device operating parameters which may be varied by the control unit may be the maximum amplitude, the frequency, or the duty cycle of the current being passed through the induction coil.

Alternatively or additionally, the device may be provided with mechanical or electromechanical means that are operable by the control unit to physically move the refill such that the susceptor is moved relative to the induced magnetic field of the induction coil. Alternatively or additionally, the device may be provided with mechanical or electromechanical means that are operable by the control unit to physically move the induction coil within the device housing such that the induced magnetic field is moved relative to the susceptor in the refill.

By configuring the assembly such that the alternating current passed through the induction coil has a frequency greater than 20 KHz the induction coil may more effectively heat up the susceptor by magnetic hysteresis. Preferably, the alternating current passed through the induction coil may be set at a frequency greater than 100 KHz, and more preferably set at a frequency of 150 KHz.

In some embodiments, the device may accommodate more than one refill thus providing the assembly with multiple reservoirs each having their own volatile fluid transport means and susceptor.

The presence of the multiple reservoirs allows more than one type of volatile fluid to be dispensed by the device by the single induction coil simultaneously.

Alternatively the device may be provided with more than one induction coil, each induction coil being associated with a separate refill whereby, in use, the induced magnetic field from one induction coil surrounds the susceptor(s) in only one refill, this may permit alternate emanation of the volatile fluid from each respective refill, this may be especially preferably when the volatile fluids are fragrances.

In other embodiments, the device may further comprise an additional magnetic susceptor configured to heat an area around the induction coil. The benefit of this additional susceptor is to ensure that the components around the induction coil are appropriately heated, for instance the core of the induction coil or members which support the induction coil, such to avoid any volatile fluid which evaporates from the one or more wicks from condensating onto these components.

According to a second aspect of the present invention, there is provided therefore a device for evaporating a volatile fluid from a detachable refill of volatile fluid comprising a reservoir for the volatile fluid, and a volatile fluid transport means to draw the fluid from the reservoir, wherein the volatile fluid transport means also has at least one magnetic susceptor having a coercivity of substantially 50 ampere/meter ($H_C$) to substantially 1500 ampere/meter ($H_C$); wherein the device comprises a magnetic induction coil configured to operate with an alternating current passed therethrough at a frequency of between substantially 20 KHz to substantially 500 KHz to induce a magnetic field, and a volatile fluid transport means receiving area containing at least one piece of heat conducting, non-magnetic metalfoil and/or deposited heat-conducting, non-magnetic metal.

According to a third aspect of the present invention, there is provided a method for evaporating a volatile fluid, comprising the steps of locating a refill comprising a reservoir for the volatile fluid, a volatile fluid transport means to draw the fluid from the reservoir toward at least one magnetic susceptor having a coercivity of substantially 50 ampere/meter ($H_C$) to substantially 1500 ampere/meter ($H_C$) in a device comprising a magnetic induction coil configured to operate with an alternating current passed therethrough at a frequency of between substantially 20 KHz to substantially 500 KHz to induce a magnetic field and a volatile fluid transport means receiving area containing at least one piece of heat conducting, non-magnetic metal foil and/or deposited heat-conducting, non-magnetic metal; generating a magnetic field through said induction coil by passing an AC current at a frequency of between substantially 20 KHz to substantially 500 KHz therethrough;

said locating of the refill in the device being such that the at least one magnetic susceptor is at least partially within the generated magnetic field and at least partially within the volatile fluid transport means receiving area;

and evaporating the volatile fluid by said at least one magnetic susceptor being heated predominately by magnetic hysteresis induced by the changing magnetic field from the induction coil to evaporate the volatile fluid from the volatile fluid transport means and by said at least one piece of heat conducting, non-magnetic metal foil and/or deposited heat-conducting, non-magnetic metal heating to resist condensation of the evaporated fluid within the device.

The device may further comprise a control unit and/or a feedback coil and the method may comprise the control unit controlling the operation of the induction coil. The method may further comprise the control unit processing an output from the feedback coil and, from this output, varying one or more operating parameters of the induction coil.

The feedback coil may be configured, in use, to change its output when one property of a susceptor is changed from refill to refill, for example if the shape or mass or material or surface area of the susceptor changes. The method may further comprise the control unit being configured to interpret the change in output from the feedback coil to determine what type of refill is within the magnetic field of the induction coil, and from this, automatically vary a property of the induction coil to apply the appropriate heating regime to each particular refill.

As the susceptor(s) gets hot, the output from the feedback coil changes. The method may further comprise the control unit interpreting the output of the feedback coil to determine a high temperature of the susceptor(s) and automatically varying a property of the induction coil to cool the susceptor.

A further use for the feedback coil in the device could be to ensure that the device is operating as efficiently as possible. The method may further comprise the control unit monitoring the output of the feedback coil to alter the duty cycle as required to ensure the current supplied through the induction coil is optimised to the particular susceptor(s) in proximity with the induction coil.

The method may comprise the control unit may comprises the steps of the control unit varying one or more of the operating parameters of the induction coil by varying one or more of: the maximum amplitude; the frequency; the duty cycle.

The method preferably includes the step of the device being operated to pass an alternating current through the induction coil with a frequency greater than 20 KHz to more effectively heat up the susceptor by magnetic hysteresis, and preferably greater than 100 KHz, and more preferably at a frequency of 150 KHz.

Preferably, substantially all of the material in the reservoir is configured to be evaporated within 5 hours of continuous actuation of the induction coil.

More preferably, substantially all of the material in the reservoir is configured to be evaporated within 3 hours of continuous actuation of the induction coil.

The invention will now be described, by example only, with reference to the accompanying drawings in which.

Figure 1:
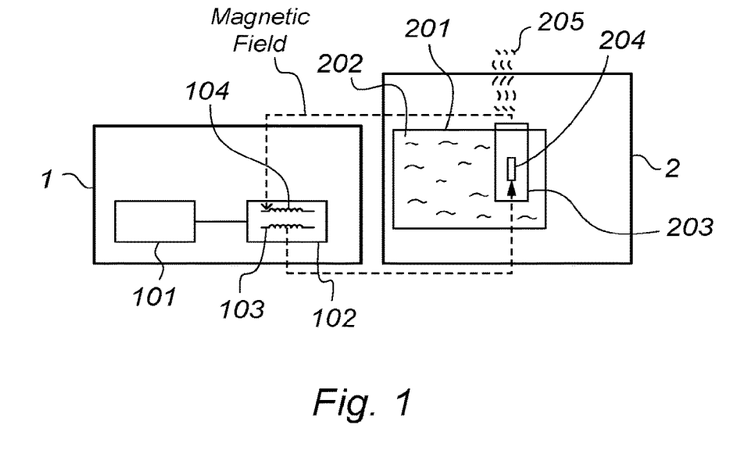
FIG. 1 shows a block diagram of an embodiment of the present invention.

FIG. 1 shows a device 1 and a refill 2. The device 1 comprises a power source 101 connected to electronic circuitry 102. Making up a part of this electronic circuitry is an induction coil 103 and an optional feedback coil 104.

The refill 2 is a separate component to the device 1. The refill 2 comprises a reservoir 201, which holds volatile fluid 202. The refill 2 also comprises a fluid transport means 203 illustrated here as a wick, which contains a susceptor 204. The susceptor is preferably in, or at least partially in, the wick 203. The wick 203 should extend beyond the reservoir 201 so that the fluid 205 which evaporates from the wick 203 can pass to the exterior of both the device 1 and the refill 2.

The power source 101 of the device 1 may for example be a connection to a mains supply, a connection to a USB docking station, or a battery.

Figure 2:
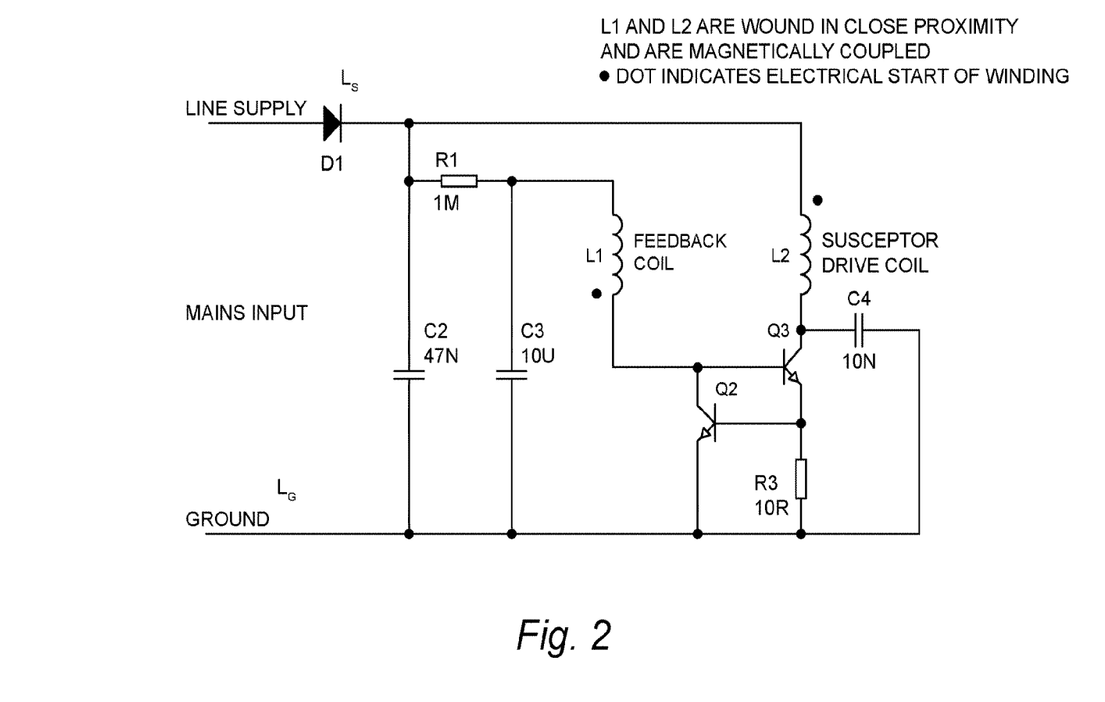
FIG. 2 shows in more detail one example of the electronic circuitry used in the embodiment shown in FIG. 1.
Figure 3:
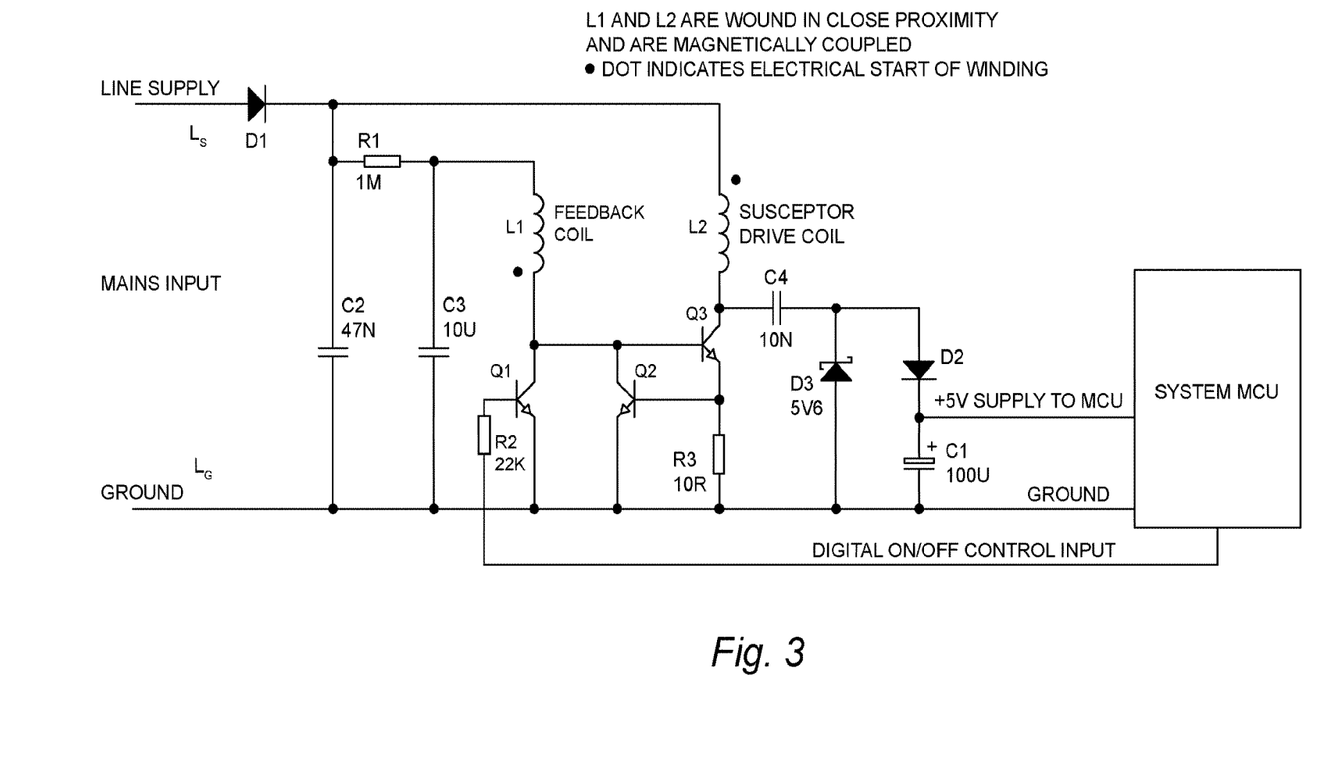
FIG. 3 shows in more detail a further example of the electronic circuitry used in the embodiment shown in FIG. 1.

The circuit diagrams shown in FIGS. 2 and 3 are examples of self-resonant/self-oscillating zero voltage switched (ZVS) converter circuits. Such circuits are well known in the art.

The ZVS circuits shown are configured to provide a high frequency magnetic field across a induction coil L2 (approximately 200 KHz). In FIG. 2, the circuit is located between a line supply $L_S$ and a ground connection $L_G$. Connected to the line supply $L_S$ is the power source 101, which provides the line supply $L_S$ with AC current. On the line supply $L_S$ is a diode D1. The circuitry also comprises the feedback coil 104, the induction coil 103, three capacitors C2; C3; C4, two resistors R1; R3, and two transistors Q2; Q3.

The component layout in FIG. 3 is similar to that of FIG. 2, except for the addition of a system microcontroller unit (MCU) or control unit, with its own power supply which feeds off the line supply $L_S$, and which is adapted from the line supply $L_S$ by conventional power stepping electronics which are not shown, an additional resistor R1, an additional capacitor C1, and first and second extra diodes D2 and D3. Preferably the additional capacitor C1 is polarised, and preferably the second additional diode D3 is a Schottky diode. The purpose of the MCU in FIG. 3 is to control the duty cycle of the ZVS converter, and hence the power being delivered through the induction coil 103.

In each of FIGS. 2 and 3, the capacitor C4 is the resonating capacitor of the ZVS circuit. The high frequency voltage present at a collector Q3 is coupled by capacitor C4 to a rectifying and regulating network comprising diodes D3 and D2, and the capacitor C1. In the case of FIG. 3, the smoothed and regulated voltage present across capacitor C1 is used to power low voltage sections of the circuit including the MCU.

Operation of the invention as shown in FIG. 1-3 will now be described.

Prior to use, the power source 101 of the device 1 must be fully charged or connected. Once the device 1 is switched on, the electronic circuitry 102 of the device 1 is then configured to pass an AC current through the induction coil 103. The circuitry 102 may be configured to continually pass an AC current through the induction coil 103, or alternatively may be configured to only pass AC current through the induction coil 103 when the refill 2 containing the susceptor 204 is located near the induction coil 103, as will be discussed.

A refill 2 as shown in FIG. 1 is connected to or docked with the device 1. To hold the refill 2 in place on the device 1, a fastening means, clip, or cradle may be provided on the device 1, as is shown for example in FIGS. 4A-6C. However the refill 2 is connected to the device 1, the main requirement is that the susceptor 204 inside the refill 2 is close enough to be heated by the induction coil 103, and to interact with the optional feedback coil 104, and aluminium foil (shown in FIGS. 4 & 5) located on the device 1, as will be discussed.

Once the refill 2 is engaged with the device 1, the susceptor 204 of the refill 2, which is positioned within the magnetic field of the induction coil 103 will begin to heat up predominately by magnetic hysteresis heating and possibly to a minor degree also by eddy current heating. As the susceptor 204 heats up, due to its proximity with the wick 203, the volatile fluid 202 inside the wick 203 also starts to heat up and vaporise for dispersion to outside of the refill 2. Preferably the susceptor 204 should be in, or at least partially in, the wick 203. This way, the wick 203 thermally insulates the susceptor 204 from the remainder of the fluid in the reservoir 201, meaning the heat emanating from the susceptor 204 is largely contained within the wick 203, and is not transmitted to the fluid reservoir 201 surrounding the wick 203.

To control how much volatile fluid 202 is dispersed at any given time, the electronic circuitry 102 from the device 1, in particular the MCU, can control the amount of current flowing through the induction coil 103, and hence control the amount of heating occurring in the susceptor 204. The current flowing through the induction coil 103 can be varied for example by increasing the duty cycle of the circuit, or by increasing the maximum current flowing through the induction coil 103.

Such control can be either by external human input, for example by an end user via a switch or dial, or preferably by the MCU in response to an output from a feedback coil 104 provided in the electronic circuitry 102, as is discussed below.

To reduce condensation within the device 1 a layer of aluminium foil 205 is located on an inner surface of the induction coil 103 that forms a chimney to direct evaporated fluid to the exterior of the device 1. The aluminium foil 205 heats up, it is suspected, by the susceptor 204 having a sufficient affinity for the induced magnetic field that it forces the magnetic field through the aluminium foil 205 which results in the foil 205 heating up thus to within 5° C. of the susceptor 204 temperature. This heating of the aluminium foil 205 reduces the likelihood for condensation within the device 1 and also promotes airflow therethrough as it creates a thermal gradient between the chimney and the air surrounding the device 1.

If a feedback coil 104 is provided, when current is flowing through the induction coil 103, the feedback coil 104 will pick up the magnetic field being emitted from the induction coil 103. When a susceptor 204 contained in a refill 2 is inserted into this magnetic field, the magnetic field will become distorted, depending on the physical properties of the susceptor, and so the signal being picked up from the feedback coil 104 will change. By electrically connecting the MCU to the feedback coil 104, the MCU can be configured to interpret the signal received from the feedback coil 104, and from this interpret what type or shape of susceptor 204 is positioned near the device 1, if any.

The feedback coil 104 can also be used as a power control means to prevent the susceptor 204 from getting too hot. As the susceptor heats up during operation, its effect on the magnetic field generated by the induction coil 103 changes. By electrically connecting the MCU to the feedback coil 104, the MCU can be configured to interpret the signal received from the feedback coil 104, and from this interpret the temperature of the susceptor 204. The MCU can then control the amount of current being passed through the induction coil 103.

Another use for the output from the feedback coil 104 by the MCU is for monitoring the form of power being supplied by the electronic circuitry. By sampling the output signal from the feedback coil 104, the MCU can be configured to vary the properties of the electronic circuitry to ensure that the alternating current being passed through the induction coil 103 is matched to the particular susceptor 204 in proximity with the induction coil 103.

If no MCU or feedback coil 104 is present in the electronics of the evaporation device, the device operates at a predetermined power level and operates in either an "on" or "off" state.

Figure 4A:
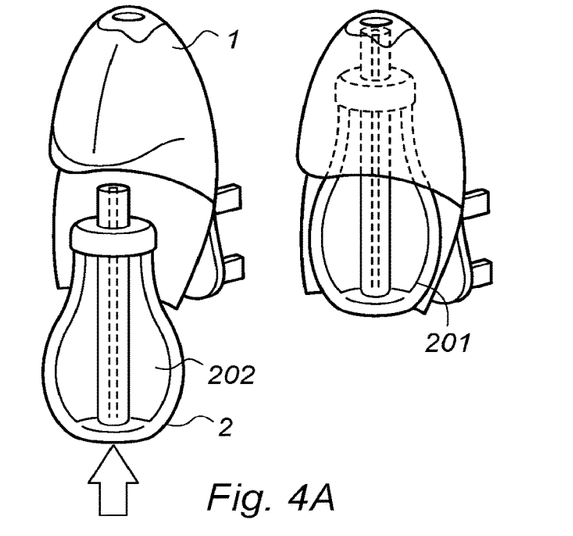
FIGS. 4A and 4B show an example layout of the invention, when configured as a device and a refill unit.
Figure 4B:
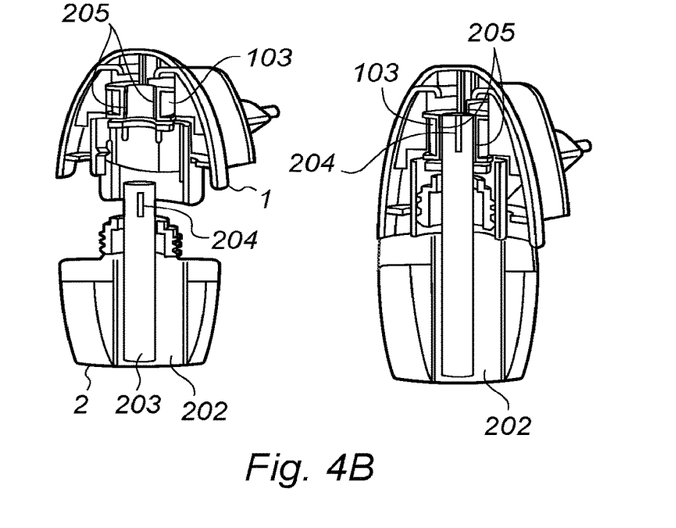

An example design of both the device 1 and refill 2 is shown in FIGS. 4A and 4B. The configuration of both the device 1 and refill 2 is largely dependent on the induction coil 103 being able to efficiently heat the susceptor 204, and if a feedback coil 104 is present, allowing this coil to interact with the magnetic fields generated by the induction coil 103. In the case of FIGS. 4A and 4B, the induction coil 103 is tubular in shape and is located such that once the refill 2 is connected with the device 1, the susceptor 204 fits inside the induction coil 103. Although not shown in FIGS. 4A and 4B, where a feedback coil 104 is also present, this could be placed in a concentric type arrangement in or around the induction coil 103.

Although only one susceptor 204 is shown in FIGS. 4A and 4B, it could be that more than one susceptor 204 is used in the wick 203.

Figure 5A:
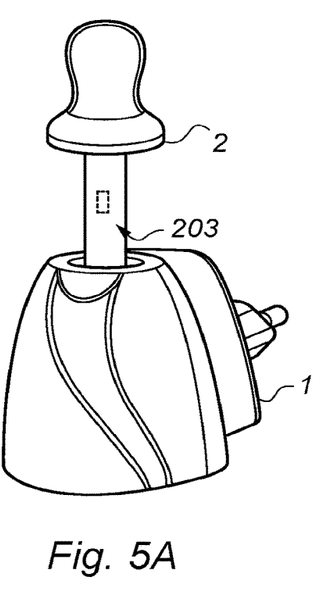
FIGS. 5A-5C show another example layout of the invention which uses a gel stick type delivery system.
Figure 5B:
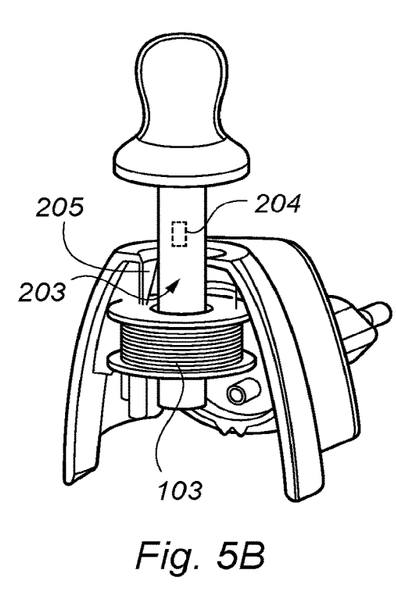
Figure 5C:
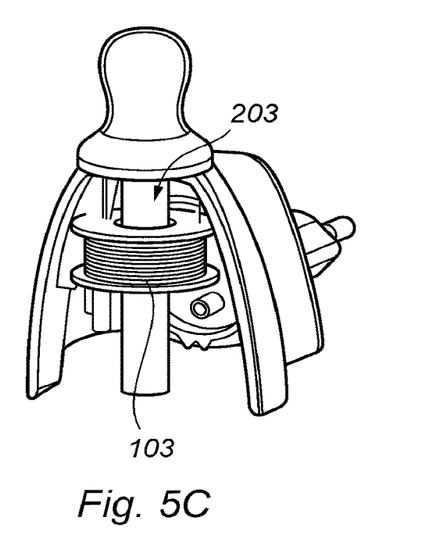

An alternative design to the evaporation device of FIGS. 4A and 4B is shown in FIGS. 5A-5C. These figures show a design which uses a gel matrix wherein the reservoir 201' and fluid transport means 203' are integral with each other and wherein the gel may be supported by a lattice material (not shown) to impart mechanical strength thereto. As fluid in the gel matrix is evaporated adjacent to the magnetic susceptor 204, the remainder of the fluid in the reservoir 201' migrates towards the susceptor 204

Figures 6A, 6B, 6C:
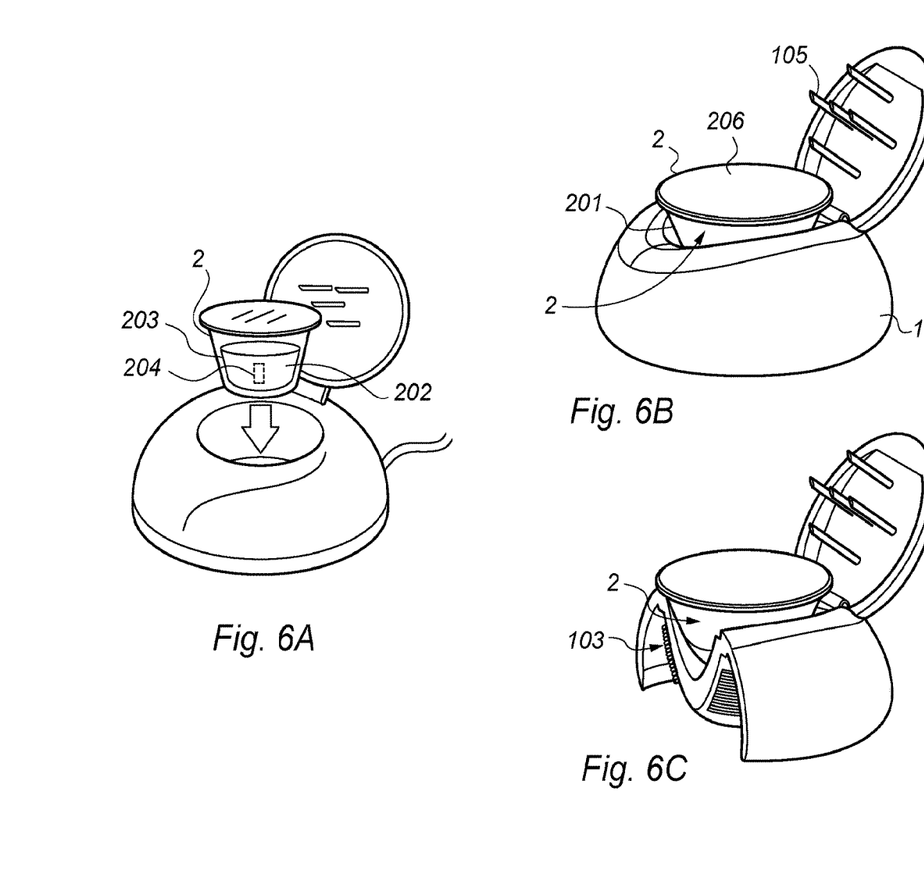
FIGS. 6A-6C show a further example layout of the invention which uses a pod type delivery system.

FIGS. 6A-6C show a further example of the evaporation device. In this embodiment, the refill 2 comprises a wick 203 which lines the inside of the pod shaped refill 2. The wick is saturated with volatile fluid 202, and is evaporated by localised heat from a susceptor 204 also located in the wick 203 on one side of the pod. The refill 2 also comprises a cover 206 which can be perforated.

The device 1 of the example shown in FIGS. 6A-6C comprises tube like perforating elements 105 which are configured to pierce the cover 206 of the refill 2 during operation of the evaporation device. The induction coil 103 on the base element 1 is located to conform to the outer shape of the refill 2.

To operate the embodiment shown in FIG. 6A-6C, a user places the refill 2 into the device 1 such that the susceptor 204 therein can interact with the induction coil 103 of the device 1. To aid with placing the refill 2 in the correct orientation, an alignment feature (not shown) could be provided on the refill 2 which locates with a corresponding feature on the device 1.

The user then closes the lid of the device 1 to cause the perforating element 105 to pierce into the cover 206. The induction coil 103 then heats the susceptor 204 of the refill 2 as previously described, causing volatile fluid 202 in the wick 203 near the susceptor 204 to evaporate and flow out through the perforating elements 105. The inner surface of the perforating elements 105 being provided with a layer of aluminium which heats to prevent condensation therein. As the volatile fluid 202 which is near the susceptor 204 evaporates, volatile fluid 202 which is located further away from the susceptor 204 is drawn towards it by capillary action as previously described.

If the volatile fluid 202 in the embodiment of FIGS. 6A-6C is in the form of a gel, then the wick 203 could be designed in the form of a lattice as described above in relation to FIGS. 5A-5C, or designed in any other shape that will support the gel.

As an optional safety feature to the design as shown in FIGS. 6A-6C, the perforating elements 105 may be configured to be made inaccessible when the device is not in use.

It will be appreciated that the designs shown in FIGS. 4A-6C could be adapted to allow the accommodation of more than one refill 2. For example, extra ports could be provided on the device 1 to allow the connection of additional refills 2. Each port on the device 1 could be provided with its own induction coil 103 such that the fluid 202 contained in each refill 2 could be heated independently of the fluid contained in the other refills 2. Alternatively, all the refills 2 could be selectively heated by a single induction coil 103 located on the device 1, using conventional time switching circuitry. Irrespective of the number of induction coils 103 or number of refills 2 used, the principle of operation would be the same as previously described.

Figure 7:
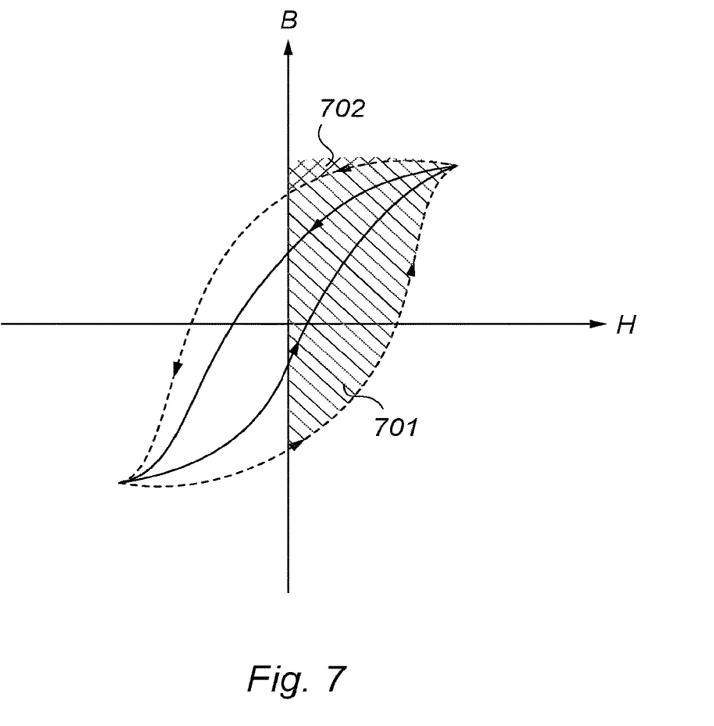
FIG. 7 shows hysteresis loops for two different susceptor materials.

Ideally the magnetic material for the magnetic susceptor should have a high hysteresis loss so that when it is repeatedly magnetised and demagnetised by an external magnetic field a relatively high proportion of the external field energy is converted into heat. The magnetic properties exhibited by such a magnetic material may be represented by a plot of flux density (B) against magnetic field strength (H) as shown in FIG. 7. Materials having relatively low hysteresis losses are typified by the solid hysteresis loop which has a small area whilst materials having relatively high hysteresis losses are typified by the dotted hysteresis loop which has a high area. The proportion of the external magnetic field energy that is converted into heat by the susceptor for each magnetic cycle is proportional to the area of the hysteresis loop corresponding to the particular magnetic material. Accordingly magnetic materials having small area hysteresis loops generate less heat when subjected to a given alternating magnetic field and function poorly as susceptor materials. Conversely magnetic materials having large area hysteresis loops generate more heat when subjected to the same alternating magnetic field and function well as susceptor materials. The area of the hysteresis loop of a magnetic material is proportional to its coercivity so that a material having a high coercivity may be particularly suitable for use as a susceptor. Such a material should have a coercivity in the range of 50-1500 ampere per meter ($H_C$).

There is an upper range to the coercivity to guard against an excessively high coercivity in order that external alternating magnetic fields may readily bring about the necessary magnetic flux reversals in the material thus preventing fine control of the heating performance via magnetic hysteresis. Such materials are known as magnetically soft materials and are distinguished thereby from the very high coercivity magnetically hard materials which are typically used in permanent magnet applications.

The invention claimed is:

1. A volatile fluid evaporating device which evaporates a volatile fluid from a detachable refill comprising a reservoir containing a volatile fluid, and a volatile fluid transport means to draw the fluid from the reservoir, wherein the volatile fluid transport means also has at least one magnetic susceptor having a coercivity of between about 50 ampere/meter ($H_c$) and about 1500 ampere/meter ($H_c$); wherein the device comprises a magnetic induction coil operable with an alternating current passed therethrough at a frequency of between about 20 KHz to about 500 KHz which induces a magnetic field, and a volatile fluid transport means receiving area containing at least one piece of heat-conducting, non-magnetic metal foil and/or deposited heat-conducting, non-magnetic metal.

2. A device according to claim 1, wherein the volatile fluid transport means receiving area is provided in the form of a chimney comprising a substantially cylindrical component open at one end adapted to receive the volatile fluid transport means and open at the other end to the environment surrounding the device.

3. A device according to claim 1, wherein the chimney is rotatable and/or movable relative to the rest of the device and is provided with one or more holes and/or windows any or all of which are arranged to promote airflow into the chimney and out into the environment surrounding the device.

4. A device according to claim 1, wherein the heat-conducting, non-magnetic metal is selected from the group consisting of aluminum, silver, gold, platinum, tungsten, magnesium and copper.

5. A device according to claim 1, wherein the heat-conducting, non-magnetic metal is aluminum, or aluminum foil.

6. A device according to claim 1, wherein the heat-conducting, non-magnetic metal foil is provided in the form of sheet foil having a thickness of between about 8 µm and about 25 µm.

7. A device according to claim 1, wherein the deposited heat-conducting, nonmagnetic metal is provided as a vacuum metalised deposit having a thickness of between about 0.1 µm and 10 µm.

8. A device according to claim 1, wherein the heat-conducting, non-magnetic metal is in contact with the inner surface of the chimney and face the volatile fluid transport means.

9. A method for evaporating a volatile fluid, comprising the steps of:
locating a refill comprising a reservoir containing the volatile fluid, a volatile fluid transport means to draw the fluid from the reservoir toward at least one magnetic susceptor having a coercivity of between about 50 ampere/meter ($H_c$) and about-1500 ampere/meter ($H_c$) in a device comprising a magnetic induction coil operable with an alternating current passed therethrough at a frequency of between about 20 KHz to about 500 KHz which induces a magnetic field and a volatile fluid transport means receiving area containing at least one piece of heat-conducting, non-magnetic metal foil and/or deposited heat-conducting, non-magnetic metal;
generating a magnetic field through said induction coil by passing an AC current at a frequency of between about 20 KHz to and about 500 KHz therethrough;
the location of the refill in the device being such that the at least one magnetic susceptor is at least partially within the generated magnetic field and at least partially within the volatile fluid transport means receiving area;
and evaporating the volatile fluid by said at least one magnetic susceptor being heated predominately by magnetic hysteresis induced by the changing magnetic field from the induction coil which evaporates the volatile fluid from the volatile fluid transport means and by said at least one piece of heat-conducting, non-magnetic metal foil and/or deposited heat-conducting, nonmagnetic metal heating to resist condensation of the evaporated fluid within the device.

* * * * *